(12) United States Patent
Yamazaki

(10) Patent No.: US 6,769,871 B2
(45) Date of Patent: Aug. 3, 2004

(54) BLOOD PUMP AND VENTRICULAR ASSIST DEVICE

(75) Inventor: Kenji Yamazaki, Tokyo (JP)

(73) Assignee: Sun Medical Technology Research Corporation, Nagano (JP)

( * ) Notice: Subject to any disclaimer, the term of this patent is extended or adjusted under 35 U.S.C. 154(b) by 0 days.

(21) Appl. No.: 10/217,959

(22) Filed: Aug. 12, 2002

(65) Prior Publication Data

US 2003/0068227 A1 Apr. 10, 2003

(30) Foreign Application Priority Data

Aug. 13, 2001 (JP) ........................................ 2001-245202

(51) Int. Cl.⁷ ................................................. F04D 7/02
(52) U.S. Cl. ........................ 415/200; 415/900; 604/6.11
(58) Field of Search ............................. 415/200, 216.1, 415/900; 416/241 R; 604/6.11

(56) References Cited

U.S. PATENT DOCUMENTS

| | | | |
|---|---|---|---|
| 5,423,886 A | 6/1995 | Arru et al. | |
| 5,562,730 A | 10/1996 | Davidson | |
| 5,711,959 A * | 1/1998 | Kohler et al. | ................ 424/423 |
| 5,924,975 A | 7/1999 | Goldowsky | |
| 6,186,665 B1 * | 2/2001 | Maher et al. | ................ 384/206 |
| 6,270,788 B1 * | 8/2001 | Koulik et al. | ................ 424/423 |
| 6,439,845 B1 * | 8/2002 | Veres | .......................... 415/206 |
| 6,583,251 B1 * | 6/2003 | Chaikof et al. | ............. 526/277 |

FOREIGN PATENT DOCUMENTS

| | | |
|---|---|---|
| EP | 0-810239 | 12/1997 |
| JP | 60-21599 | 5/1985 |
| JP | 6-313009 | 8/1994 |
| JP | 7-116245 | 5/1995 |
| JP | 8-000723 | 1/1996 |
| JP | 9-131397 | 5/1997 |
| JP | 2890316 | 2/1999 |

* cited by examiner

*Primary Examiner*—Ninh H. Nguyen
(74) *Attorney, Agent, or Firm*—Hogan & Hartson, LLP

(57) ABSTRACT

The blood pump according to the present invention comprises a casing having a blood inlet and a blood outlet, and an impeller for circulating blood by rotating inside the casing, wherein both the casing's and the impeller's surfaces in contact with blood are formed of a biocompatible metal, and onto the surfaces in contact with blood a coating film of a hemocompatible material comprising a phospholipid polymer is formed. According to the present invention, the blood pump effectively suppresses the development of thrombi without activating blood coagulation factors such as thrombocites (blood platelets) in the blood, thanks to a coating film of a hemocompatible material made of a phospholipid polymer being formed onto the surfaces in contact with blood of the casing and the impeller composing the main part of the blood pump.

5 Claims, 3 Drawing Sheets

| Usage | Acute Phase | Chronic Phase |
|---|---|---|
| First Usage | Use the Blood Pump (Administer Anticoagulant) | D'ont Use the Blood Pump |
| Second Usage | Use the Blood Pump (D'ont Administer Anticoagulant) | D'ont Use the Blood Pump |
| Third Usage | Use the Blood Pump (D'ont Administer Anticoagulant) | Use the Blood Pump (D'ont Administer Anticoagulant) |
| Forth Usage | Use the Blood Pump (D'ont Administer Anticoagulant) | Use the Blood Pump (Administer Anticoagulant) |

FIG.2

BLOOD PUMP AND VENTRICULAR ASSIST DEVICE

BACKGROUND OF THE INVENTION

1. Field of the Invention

The present invention relates to a blood pump and a ventricular assist device. More particularly, the invention relates to a blood pump and a ventricular assist device capable of effectively suppressing the development of thrombi.

2. Related Art

Blood pumps for assisting the circulation that are used in case of cardiogenic shocks or acute myocardial infarction during or after open heart surgery need to operate continuously for the period required for the patient's cardiac function to recover.

Pulsatile type blood pumps are widely used for assisting the circulation. However, the pulsatile type blood pumps have a insufficient long term reliability, as a result of the polymer used for materials of the pulsatile type blood pumps. Non-pulsatile blood pumps, such as Rotaly blood pumps, made of metal have a long term reliability compared to pulsatile type blood pumps. However, there exist a demand or need to improve thrombus suppression function. Coagulation factors in the blood such as thrombocytes are activated as a result of blood in contact with foreign materials, and thrombus formation has some effects of performance of the blood pumps.

To fulfill this demand, Japanese laid-open application JPH7-116245A discloses an invention that consists in coating all blood pump parts in contact with blood with a hemocompatible material, such as antithrombogenic material, made of a phospholipid polymer.

According to this prior art invention, coagulation factors in the blood such as thrombocytes will not be activated and the development of thrombi will be effectively suppressed, as a result of all parts in contact with blood being coated with a hemocompatible material made of a phospholipid polymer. This enables a blood pump capable of long term continuous operation over two weeks or more.

However, if thrombi develop inside the blood pump during or after open heart surgery, the blood pump might stop operating. Therefore, it has been common practice up to now to administer the patient with an anticoagulant when making use of a blood pump, leading to an increased risk of hemorrhage complications during the postoperative acute phase (a phase or period lasting for about one month after surgery during which there is a high risk of hemorrhage).

An object of the present invention is to solve these problems by providing a blood pump and a ventricular assist device that have a considerably increased thrombus suppression function compared to current blood pumps, in order to allow long term continuous operation of the blood pump even without any administration of anticoagulants to the patient, and thereby enable the suppression of hemorrhage complications during the postoperative acute phase.

SUMMARY OF THE INVENTION

The blood pump according to the one aspect of the present invention comprises a casing having a blood inlet and a blood outlet, and an impeller for circulating blood by rotating inside the casing, wherein both the casing's and the impeller's surfaces in contact with blood are formed of a biocompatible metal, and onto the surfaces in contact with blood a coating film of a hemocompatible material comprising a phospholipid polymer is formed.

The blood pump according to the present invention effectively suppresses the development of thrombi without activating blood coagulation factors such as thrombocites (blood platelets) in the blood, thanks to a coating film of a hemocompatible material made of a phospholipid polymer being formed onto the surfaces in contact with blood of the casing and the impeller composing the main part of the blood pump.

The blood pump of the present invention furthermore maintains the function of effectively suppressing the development of thrombi without activating blood coagulation factors such as thrombocites (blood platelets) in the blood, even if a part of the coating film of a hemocompatible material made of a phospholipid polymer should for elute or come off with long term continuous operation, as the metal below is a biocompatible metal, that is, the surfaces in contact with blood of the casing and impeller composing the main part of the blood pump are made of a biocompatible metal.

Therefore, the blood pump according to the present invention has a considerably increased thrombus suppression function compared to current blood pumps, thus allowing long term continuous operation of the blood pump even without any administration of anticoagulants to the patient, and as a result, enabling the suppression of hemorrhage complications during the postoperative acute phase.

Furthermore, as the blood pump according to the present invention has a considerably increased thrombus suppression function compared to current blood pumps, thus allowing long term continuous operation for 30 days or more, it can be used well into the postoperative chronic phase (the chronic phase is the phase or period following the acute phase of about one month after the surgery in which the risk of hemorrhage is reduced as compared to the risk during the acute phase).

During the chronic phase, as the threat of hemorrhage complication development decreases, anticoagulant administration in combination with the use of the blood pump becomes a rational choice, thereby assuring even longer term continuous operation.

In this context, "the surfaces in contact with blood are formed of a biocompatible metal" includes both of the following interpretations, either the whole component, or only the parts in proximity of the surfaces are formed of a biocompatible metal.

According to the present invention, a similar advantageous effect can be obtained irrespective of whether the blood pump is of the centrifugal type or of the axial flow type.

The blood pump generally comprises a pump part and a drive part, and among the partition parts to separate the two, the pump side part (also called: pump base part) also belongs to the above-mentioned casing.

The hemocompatible material comprising a phospholipid polymer also includes such ones, wherein not only all units but also only some part of the units include a phospholipid.

In the blood pump according to the present invention, the biocompatible metal preferably is pure titanium or a titanium alloy, the metals being highly suited for living bodies. As a titanium alloy, Ti-6AI-4V alloy (especially ELI (Extra Low Interstitial) glade) with 6% aluminum and 4% Vanadium added to the titanium is preferably used.

In the blood pump according to the present invention, the biocompatible metal preferably is pure titanium.

In the blood pump according to the present invention, the arithmetic mean of the surface roughness Ra of both the casing's and the impeller's surfaces in contact with blood preferably is 0.5 μm or less. The arithmetic mean of the surface roughness Ra of the surfaces in contact with blood of 0.5 μm or less leads to a smooth coating of a material suited for blood comprising a phospholipid onto its surface, thereby even more effectively suppressing the development of thrombi as the blood flow will flow smoothly and sedimentation will be prevented. From this point of view, it is more preferable for the arithmetic mean of the surface roughness Ra of both the casing's and the impeller's surfaces in contact with blood to be 0.2 μm or less.

In the blood pump according to the present invention, preferably a coating film of a hemocompatible material comprising a phospholipid polymer is also formed onto the parts in contact with blood other than those of the casing and the impeller.

By also forming a coating film of a hemocompatible material comprising a phospholipid polymer onto these other parts in contact with blood, as for example onto a mechanical seal, the suppression function of thrombi development can be further increased.

In the blood pump according to the present invention, the arithmetic mean of the surface roughness Ra of these other surfaces in contact with blood preferably is 0.5 μm or less. The arithmetic mean of the surface roughness Ra of the other surfaces in contact with blood of 0.5 μm or less leads to a smooth coating of a hemocompatible material comprising a phospholipid onto its surface, thereby even more effectively suppressing the development of thrombi as the blood flow will flow smoothly and sedimentation will be prevented. From this point of view, it is more preferable for the arithmetic mean of the surface roughness Ra to be 0.2 μm or less.

In the blood pump according to the present invention, the thickness of the coating film preferably is 0.5 μm or less. A coating film thickness of 0.5 μm or less leads to a smooth coating film, thereby even more effectively suppressing the development of thrombi as the blood flow will flow smoothly and sedimentation will be prevented.

In the blood pump according to the present invention, the impeller preferably is an open vane type impeller. If the impeller is an open vane type impeller the energy exchange efficiency is slightly reduced compared to closed vane type and semi-closed vane type impellers, but the blood flow will get even smoother and unlikely to accumulate. Therefore, the development of thrombi is even more effectively suppressed.

In the blood pump according to the present invention, the hemocompatible material comprising a phospholipid polymer preferably is a (meth)acryloyloxy lower alkylphosphorylcholine copolymer as it is very well suited for contact with blood.

In the blood pump according to the present invention, the (meth)acryloyloxy lower alkylphosphorylcholine copolymer preferably is a copolymer of a (meth)acryloyloxy lower alkylphosphorylcholine and a (meth)acrylic acid ester. Even though a (meth)acryloyloxy lower alkylphosphorylcholine homopolymers would be even better suited for contact with blood, there is a concern as it is highly hydrophilic and therefore easily elutes. By adding a (meth)acrylic acid ester, the extent of hydrophilic properties is adjusted, and while keeping good blood suitability, the coating film is made robust against elution. As a result of experiments it became understood, that "(meth)acryloyloxy lower alkylphosphoryl- choline to (meth)acrylic acid ester" is preferably around "30% to 70%" in adding molar ratio.

In the blood pump according to the present invention, the (meth)acryloyloxy lower alkylphosphorylcholine preferably is a 2-methcryloyloxyethyl-phosphorylcholine having the following formula, for being especially highly suited for blood.

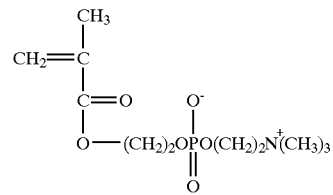

Formula 1

In the blood pump according to the present invention, the (meth)acrylic acid ester preferably is a butyl methacrylate. This is because the hydrophilic properties are easy to adjust, and the mechanical strength is easy to preserve. Furthermore, butyl methcrylate is desirable whether it be as n-butyl methcrylate or as isobutyl methcrylate.

In the blood pump according to the present invention, the coating film is preferably formed by coating a solution containing a copolymer of the (meth)acryloyloxy lower alkylphosphorylcholine and the (meth)acrylic acid ester onto the surfaces in contact with blood.

The blood pump according to the other aspect of the present invention comprises: a casing having a blood inlet and a blood outlet; and an open vane type impeller for circulating blood by rotating inside the casing, wherein both the casing's and the impeller's surfaces in contact with blood are formed of pure titanium, and onto the casing's and impeller's and other parts' surfaces in contact with blood a coating film of a (meth)acryloyloxy lower alkylphosphorylcholine copolymer is formed.

In this way, the blood pump of the present invention's thrombi development suppression function is further increased compared to current blood pumps, as the surfaces in contact with blood of the main parts of the blood pump are formed of pure titanium, and, in addition to these surfaces in contact with blood for example onto other parts like a mechanical seal's surface in contact with blood a coating film of a (meth)acryloyloxy lower alkylphosphorylcholine copolymer is formed, and in addition, because the impeller is an open vane type impeller.

The ventricular assist device of the one aspect of the present invention comprises: a blood pump comprising a casing having a blood inlet and a blood outlet; and an impeller for circulating blood by rotating inside the casing, wherein both the casing's and the impeller's surfaces in contact with blood are formed of a biocompatible metal, and onto the surfaces in contact with blood a coating film of a hemocompatible material comprising a phospholipid polymer is formed;

an inlet side artificial blood vessel connected to the blood pump;

a cannula connected to the inlet side artificial blood vessel; and an outlet side artificial blood vessel connected to the blood pump, wherein the cannula is formed of a biocompatible metal, and onto the cannula's surfaces in contact with blood a coating film of a hemocompatible material comprising a phospholipid polymer is formed.

Therefore, the ventricular assist device of the one aspect of the present invention, as mentioned above, features a blood pump with a high thrombi development suppression function compared to current blood pumps. Furthermore, in the cannula the thrombi development suppression function has also been increased. Therefore, the ventricular assist device of the present invention is a very outstanding ventricular assist device that effectively prevents the development of thrombi.

The ventricular assist device of the other aspect of the present invention comprises: a blood pump comprising a casing having a blood inlet and a blood outlet, and an open vane type impeller for circulating blood by rotating inside the casing, wherein both the casing's and the impeller's surfaces in contact with blood are formed of pure titanium, and onto the casing's and impeller's and other parts' surfaces in contact with blood a coating film of a (meth) acryloyloxy lower alkylphosphorylcholine copolymer is formed;

an inlet side artificial blood vessel connected to the blood pump;

a cannula connected to the inlet side artificial blood vessel; and an outlet side artificial blood vessel for outlet side use connected to the blood pump, wherein the cannula is formed of a biocompatible metal, and onto the cannula's surfaces in contact with blood a coating film of a hemocompatible material comprising a phospholipid polymer is formed.

Therefore, the ventricular assist device of the other aspect of the present invention, as mentioned above, features a blood pump with a high thrombi development suppression function compared to current blood pumps. Furthermore, in the cannula the thrombi development suppression function has also been increased. Therefore, the ventricular assist device of the present invention is a very outstanding ventricular assist device that effectively prevents the development of thrombi.

BRIEF DESCRIPTION OF THE DRAWINGS

FIG. 2 is for explaining the functioning of a blood pump according to the first embodiment of the present invention

DESCRIPTION OF THE PREFERED EMBODIMENTS

Figure 1:
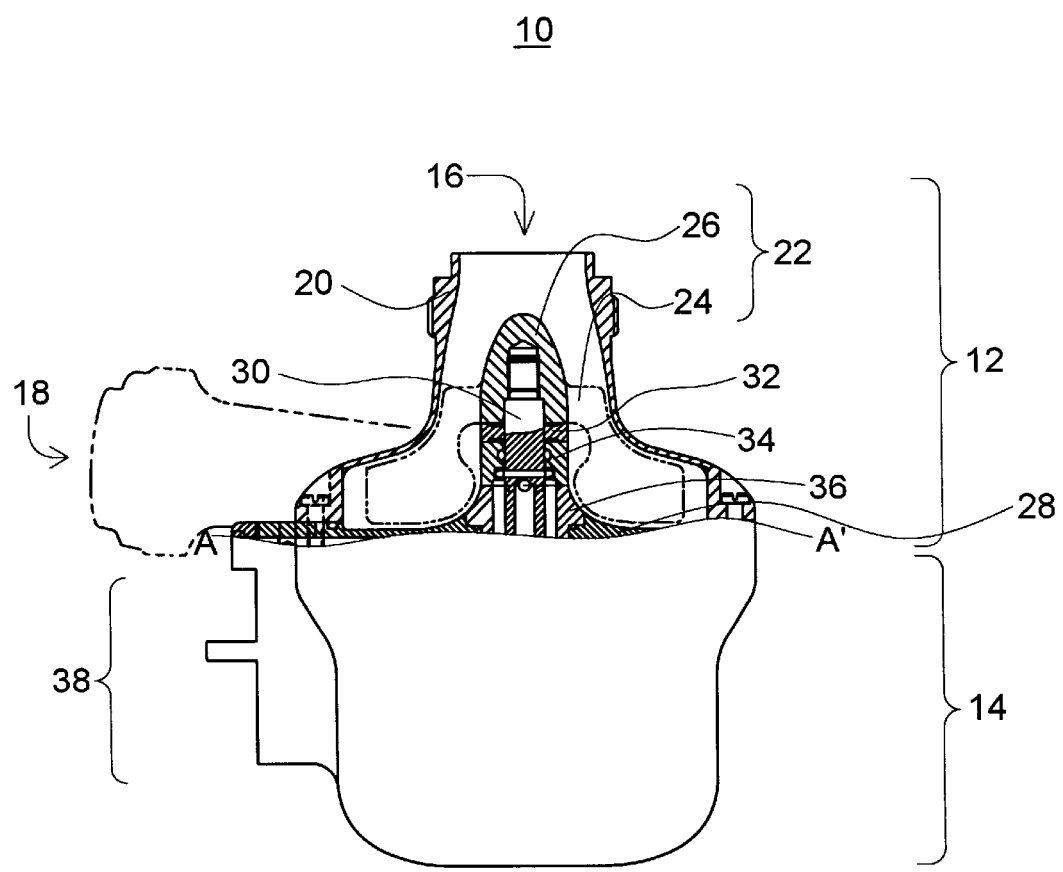
FIG. 1 shows the composition of a blood pump according to a first embodiment of the present invention.

Below, embodiments of the present invention will be explained in detail with reference to the drawings.
First Embodiment FIG. 1 shows the composition of the blood pump 10 of a first embodiment of the present invention. The blood pump 10 of the first embodiment has a pump part 12 and a drive part 14. In FIG. 1, the pump part 12 (a part shown above the line A–A') is shown in a cross sectional view and the drive part 14 (a part shown below the line A–A') is shown in a front view.

Pump part 12 includes a casing 20 having a blood inlet 16 and a blood outlet 18, and an impeller 22 for circulating blood by rotating inside this casing 20. The impeller 22 comprises a vane 24 and a boss 26, and as clearly shown in FIG. 1, is an impeller 22 of the open vane type without shroud. Further, in FIG. 1, the depiction of vane 24 is not the real cross-section, but rather the cross section of the rotating body formed by the rotation of the vane 24.

The drive part 14 includes a motor (not shown) for rotating the impeller 22 via a shaft 30, a seal liquid circulation mechanism (not shown) for circulating the seal liquid, and an interface part 38 to an external controller (not shown) controlling the operation of this blood pump 10.

The pump part 12 and the drive part 14 are separated by a partition part 28, its upper part becoming the pump's base part. The blood inside pump part 12 is hindered from progressing towards the drive part 14 by a mechanical seal and the effect of the seal liquid being supplied to this mechanical seal. The mechanical seal is composed of a mating ring (fixed ring) 36 comprising ceramics (SiC), a seal ring (rotating ring) 34 comprising carbon, and a cushion ring (the other rotating ring) 32 comprising silicone rubber. The seal liquid is circulated by the effect of the seal liquid circulation mechanism (not shown) between the drive part 14 and the reservoir inside the external controller. The seal liquid is supplied to the mechanical seal (particularly the sliding face of the mating ring 36 and the seal ring 34) by passing through the cavity inside the shaft 30 and the groove between shaft and bearing.

In the blood pump 10 of the first embodiment, the surfaces in contact with blood of both the casing 20 (including the pump base part composing the upper part of the partition part 28) and the impeller 22 are of pure titanium, and the arithmetic mean of the surface roughness Ra of these surfaces in contact with blood is 0.2 $\mu$m or below. The measurement of Ra was carried out by using a Surface Finish and Form Measurement device of Taylor-Hobson Co. (Form Talysurf S-2) (England), with a measurement length of 5 mm (or the maximum length available for measurement in case of a measurable range of 5 mm or less) and a cut-off length of 0.8 mm.

Onto these surfaces in contact with blood a coating film of a copolymer of 2-methcryloyloxyethylphosphorylcholine and butyl methacrylate is formed. Further, in the blood pump 10 of the first embodiment, onto the surfaces of parts in contact with blood other than those of the casing's and the impeller's (for example, the mating ring 36, seal ring 34, and cushion ring 32, all composing the mechanical seal) a coating film of a copolymer of 2-methcryloyloxyethylphosphorylcholine and butyl methacrylate is also formed, their surfaces' roughness Ra being 0.5 $\mu$m or below.

Above-mentioned coating film is formed by coating the surfaces in contact with blood with an ethanol solution (MPC solution) containing 0.5% by weight of a copolymer of 30 mol % 2-methacryloyloxyethylphosphorylcholine and 70 mol % butyl methacrylate (NOF Corporation). The coating film's thickness is 0.5 $\mu$m or below. The coating is carried out by the method of dipping the parts before assembly into above-mentioned MPC solution, then letting the solution drip-off sufficiently and finally wind drying or decompression drying them. Further, the coating may also be carried out by the method of circulating above-mentioned MPC solution through the blood pump after assembly, followed by wind drying or decompression drying, or by other methods.

The results of the experiments on animals confirmed the possibility of the blood pump 10 according to the first embodiment to operate continuously for 30 days or more without any administration of anticoagulants, and the considerable increase of the thrombi development suppression function as compared to current blood pumps.

FIG. 2 explains the functioning of blood pump 10 according to the first embodiment of the present invention. The blood pump 10 according to the present invention, firstly, as shown in the uppermost line of FIG. 2, may be used in the same way as current common blood pumps (that is to say, use while administering anticoagulants during the postoperative acute phase (First Usage)). With the blood pump 10 according to the present invention, because the development of thrombi suppression function is further increased as compared to current blood pumps, this first way of use also allows to extremely powerfully suppress the development of thrombi.

Secondly, the blood pump 10 according to the present invention, because the development of thrombi suppression function is further increased as compared to current blood pumps, as shown in the second line of FIG. 2, may be used without any administering of anticoagulants during the postoperative acute phase (Second Usage)). In this way, as the blood pump 10 according to the present invention may be used omitting the administering of anticoagulants during the postoperative acute phase, hemorrhage complications during the postoperative acute phase may be suppressed.

Thirdly, the blood pump 10 according to the present invention, because the development of thrombi suppression function is further increased as compared to current blood pumps, as shown in line 3 of FIG. 2, allows the use without administering anticoagulants not only during the postoperative acute phase but also continuing into and during the postoperative chronic phase (Third Usage). In this way, the blood pump 10 according to the present invention, during the acute and chronic postoperative period the administering of anticoagulants may be omitted, thereby allowing the suppression of hemorrhage complications over a long period of time after the operation.

Fourthly, the blood pump 10 according to the present invention, because the development of thrombi suppression function is further increased as compared to current blood pumps, as shown in line 4 of FIG. 2, may be used by not administering anticoagulants during the acute postoperative period, but administering anticoagulants during the chronic postoperative period (Fourth Usage). This is, because during the postoperative chronic phase the risk of developing hemorrhage complications is low in spite of anticoagulant administration. In this way, the blood pump 10 according to the present invention, during the acute postoperative period the administering of anticoagulants may be omitted, and during the chronic postoperative period the administering anticoagulants may be conducted, thereby allowing the suppression of hemorrhage complications over a long period of time after the operation.

Second Embodiment

Figure 3:
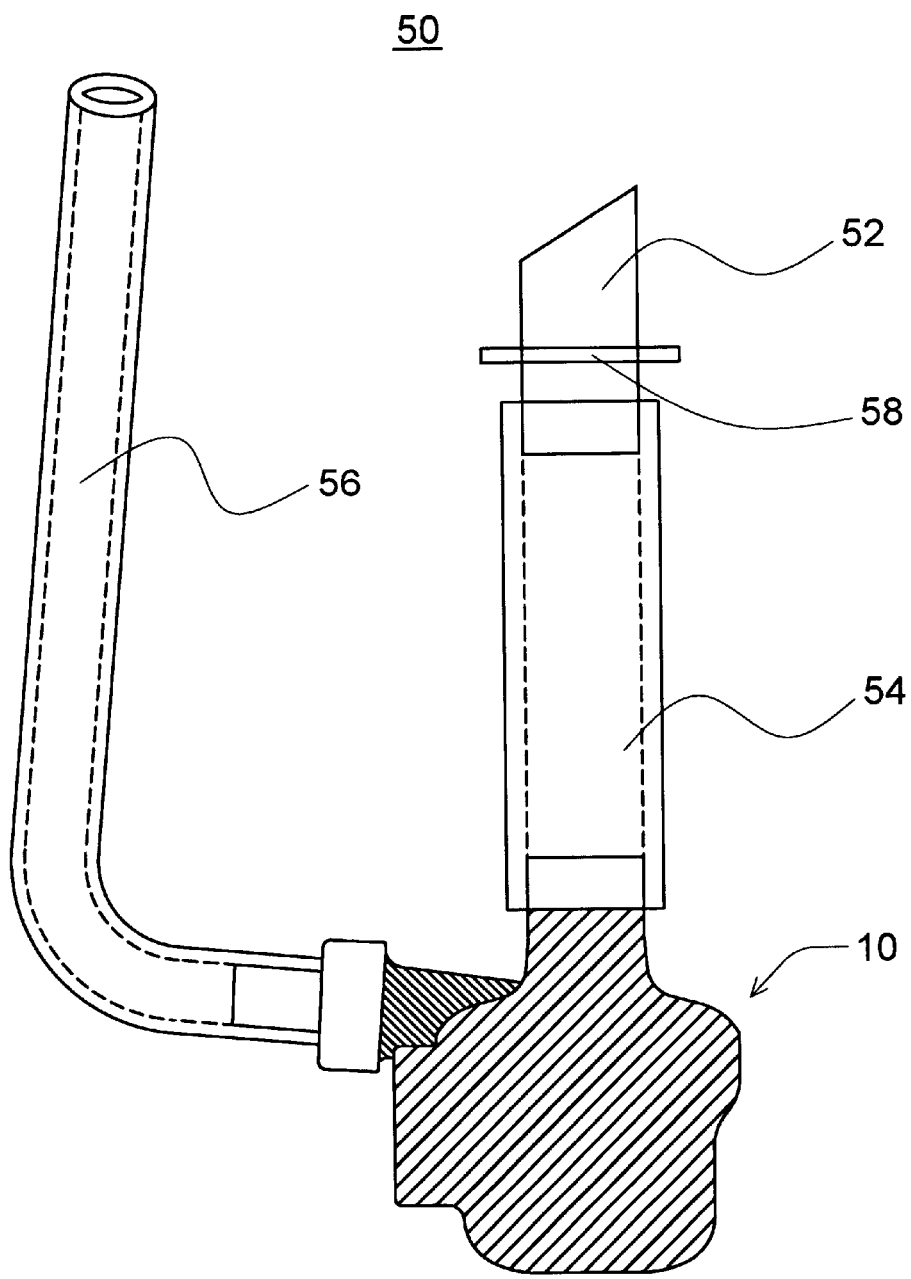
FIG. 3 shows the composition a ventricular assist device according to a second embodiment of the present invention.

FIG. 3 shows the composition of a ventricular assist device according to a second embodiment of the present invention. This ventricular assist device 50 has the blood pump 10 of the first embodiment, an inlet side artificial blood vessel 54 connected to the blood pump 10, a cannula 52 connected to the inlet side artificial blood vessel 54, and an outlet side artificial blood vessel 56 connected to the blood pump 10. Furthermore, the cannula 52 is of pure titanium, and onto the surface of the cannula 52, a coating has been carried out of a copolymer of 2-methacryloyloxyethylphosphorylcholine and butyl methacrylate. In the periphery of the cannula, a felt 58 is provided in order to sew the cannula on the apex cordis.

The ventricular assist device 50 according to the second embodiment comprises a blood pump 10 according to the first embodiment having a considerably increased thrombi development suppression function compared to current blood pumps, a cannula 52 having a considerably increased thrombi development suppression function compared to current cannulae, and therefore has a considerably increased thrombi development suppression function compared to current ventricular assist devices, thereby allowing continuous operation of the ventricular assist device over a long period of time even without administration of anticoagulants to the patient.

Third Embodiment

The blood pump according to the third embodiment is an axial flow type blood pump (not shown). This axial flow type blood pump also has a casing having a blood inlet and a blood outlet, and an impeller for circulating the blood by rotating inside the casing. Further, both the casing's and the impeller's surfaces in contact with blood are formed of pure titanium, and onto these surfaces a coating of a copolymer of 2-methacryloyloxyethylphosphorylcholine and butyl methacrylate is formed.

The blood pump according to the third embodiment also has a considerably increased thrombi development suppression function compared to current axial flow type blood pumps, and as a result, the blood pump may be operated continuously over a long period of time even without administration of anticoagulants to the patient.

Above, the present invention has been explained with reference to non-pulsatile type blood pumps, but also with reference to pulsatile type blood pumps, the thrombi development suppression function may be considerably increased by forming a coating film of a hemocompatible material of a phospholipid polymer onto the surfaces in contact with blood, with the pump part's main parts' surfaces in contact with blood being of a biocompatible metal.

What is claimed is:

1. A blood pump comprising:

a casing having a blood inlet and a blood outlet; and an impeller for circulating blood by rotating inside the casing, wherein both the casing's and the impeller's surfaces in contact with blood are formed of a biocompatible metal, and onto the surfaces in contact with blood a coating film of a hemocompatible material comprising a phospholipid polymer is formed, wherein the arithmetic mean of the surface roughness Ra of both the casing's and the impeller's surfaces in contact with blood is 0.5 $\mu$m or less.

2. A blood pump comprising:

a casing having a blood inlet and a blood outlet; and an impeller for circulating blood by rotating inside the casing, wherein both the casing's and the impeller's surfaces in contact with blood are formed of a biocompatible metal, and onto the surfaces in contact with blood a coating film of a hemocompatible material comprising a phospholipid polymer is formed, wherein onto the parts in contact with blood other than those of the casing and the impeller a coating film of a hemocompatible material comprising a phospholipid polymer is also formed, and wherein the arithmetic mean of the surface roughness Ra of these other parts' surfaces in contact with blood is 0.5 $\mu$m or less.

3. A blood pump comprising:

a casing having a blood inlet and a blood outlet; and an impeller for circulating blood by rotating inside the casing, wherein both the casing's and the impeller's surfaces in contact with blood are formed of a biocompatible metal, and onto the surfaces in contact with blood a coating film of a hemocompatible material comprising a phospholipid polymer is formed, wherein the thickness of the coating film is 0.5 μm or less.

4. A ventricular assist device, comprising:

a blood pump comprising a casing having a blood inlet and a blood outlet, and an impeller for circulating blood by rotating inside the casing, wherein both the casing's and the impeller's surfaces in contact with blood are formed of a biocompatible metal, and onto the surfaces in contact with blood a coating film of a hemocompatible material comprising a phospholipid polymer is formed;

an inlet side artificial blood vessel connected to the blood pump;

a cannula connected to the inlet side artificial blood vessel; and an outlet side artificial blood vessel connected to the blood pump, wherein the cannula is formed of a biocompatible metal, and onto the cannula's surfaces in contact with blood a coating film of a hemocompatible material comprising a phospholipid polymer is formed.

5. A ventricular assist device, comprising:

a blood pump comprising a casing having a blood inlet and a blood outlet, and an open vane type impeller for circulating blood by rotating inside the casing, wherein both the casing's and the impeller's surfaces in contact with blood are formed of pure titanium, and onto the casing's and impeller's and other parts' surfaces in contact with blood a coating film of a (meth) acryloyloxy lower alkylphosphorylcholine copolymer is formed;

an inlet side artificial blood vessel connected to the blood pump;

a cannula connected to the inlet side artificial blood vessel; and an outlet side artificial blood vessel connected to the blood pump, wherein the cannula is formed of a biocompatible metal, and onto the cannula's surfaces in contact with blood a coating film of a hemocompatible material comprising a phospholipid polymer is formed.

* * * * *